(12) United States Patent
Erbel et al.

(10) Patent No.: US 7,959,662 B2
(45) Date of Patent: Jun. 14, 2011

(54) ENDOVASCULAR PROSTHESIS

(76) Inventors: Raimund Erbel, Essen (DE); Donald R. Ricci, Vancouver (CA); Ian M. Penn, Vancouver (CA); George A. Shukov, Los Altos Hills, CA (US)

( * ) Notice: Subject to any disclaimer, the term of this patent is extended or adjusted under 35 U.S.C. 154(b) by 0 days.

(21) Appl. No.: 11/459,554

(22) Filed: Jul. 24, 2006

(65) Prior Publication Data

US 2006/0287714 A1    Dec. 21, 2006

Related U.S. Application Data

(63) Continuation of application No. 10/416,926, filed on Dec. 23, 2003, now abandoned.

(51) Int. Cl.
*A61F 2/06* (2006.01)
(52) U.S. Cl. .............. 623/1.13; 623/1.15; 623/1.17
(58) Field of Classification Search ............ 623/1.16, 623/1.39, 1.15; *A61F 02/06*
See application file for complete search history.

(56) References Cited

U.S. PATENT DOCUMENTS

| | | | | |
|---|---|---|---|---|
| 5,064,435 | A | * | 11/1991 | Porter .................. 623/23.7 |
| 5,540,713 | A | * | 7/1996 | Schnepp-Pesch et al. ... 623/1.18 |
| 5,693,088 | A | * | 12/1997 | Lazarus .................. 623/1.35 |
| 5,879,370 | A | * | 3/1999 | Fischell et al. ............ 623/1.16 |
| 5,951,599 | A | | 9/1999 | McCrory |
| 6,051,020 | A | * | 4/2000 | Goicoechea et al. ....... 623/1.35 |
| 6,123,723 | A | | 9/2000 | Konya |
| 6,152,956 | A | * | 11/2000 | Pierce .................... 623/1.13 |
| 6,231,597 | B1 | | 5/2001 | Deem et al. |
| 6,235,823 | B1 | | 5/2001 | Ikeda et al. |
| 6,290,720 | B1 | * | 9/2001 | Khosravi et al. ........... 623/1.13 |
| 6,309,414 | B1 | * | 10/2001 | Rolando et al. ............ 623/1.15 |
| 6,451,052 | B1 | * | 9/2002 | Burmeister et al. ........ 623/1.16 |
| 6,497,724 | B1 | * | 12/2002 | Stevens et al. ............ 623/1.15 |
| 6,530,950 | B1 | | 3/2003 | Alvarado et al. |
| 6,730,119 | B1 | | 5/2004 | Smalling |

FOREIGN PATENT DOCUMENTS

FR          2 756 173          5/1998
WO       WO 00/53119 A1    9/2000

* cited by examiner

*Primary Examiner* — David Isabella
*Assistant Examiner* — Jason-Dennis Stewart
(74) *Attorney, Agent, or Firm* — Katten Muchin Rosenman LLP (57) ABSTRACT

A endovascular prosthesis for implantation in a body passageway. The prosthesis comprises a tubular wall which is: (i) movable between a first longitudinal length and a second longitudinally length, and (ii) radially expandable for implantation of the prosthesis in the body passageway. In one embodiment, the tubular wall has a longitudinally length which is variable by an "accordion"-like action. In another embodiment, the tubular wall has a longitudinally length which is variable by an "telescoping"-like action. The longitudinal length of the tubular wall may be varied in vivo to optimize deployment of the endovascular prosthesis.

31 Claims, 9 Drawing Sheets

Figure 1

FIG.2a. CLASS 1.

FIG.2b. CLASS 2

FIG.2d. CLASS 4

FIG.2c. CLASS 3

FIG.2e. CLASS 5

ENDOVASCULAR PROSTHESIS

CROSS REFERENCE TO RELATED APPLICATIONS

This is a continuation of U.S. patent application Ser. No. 10/416,926, filed Dec. 23, 2003 now abandoned, the entire contents of which are incorporated herein by reference.

TECHNICAL FIELD

In one of its aspects, the present invention relates to an endovascular prosthesis. In another of its aspects, the present invention relates to a method of treating an aortic disease condition in a patient.

BACKGROUND ART

Stents are generally known. Indeed, the term "stent" has been used interchangeably with terms such as "intraluminal vascular graft" and "expandable prosthesis". As used throughout this specification the term "stent" is intended to have a broad meaning and encompasses any expandable prosthetic device for implantation in a body passageway (e.g., a lumen or artery).

In the past ten years, the use of stents has attracted an increasing amount of attention due the potential of these devices to be used in certain cases, as an alternative to surgery. Generally, a stent is used to obtain and maintain the patency of the body passageway while maintaining the integrity of the passageway. As used in this specification, the term "body passageway" is intended to have a broad meaning and encompasses any duct (e.g., natural or iatrogenic) within the human body and can include a member selected from the group comprising: blood vessels, respiratory ducts, gastrointestinal ducts and the like.

Stent development has evolved to the point where the vast majority of currently available stents rely on controlled plastic deformation of the entire structure of the stent at the target body passageway so that only sufficient force to maintain the patency of the body passageway is applied during expansion of the stent.

Generally, in many of these systems, a stent, in association with a balloon, is delivered to the target area of the body passageway by a catheter system. Once the stent has been properly located (for example, for intravascular implantation the target area of the vessel can be filled with a contrast medium to facilitate visualization during fluoroscopy), the balloon is expanded thereby plastically deforming the entire stricture of the stent so that the latter is urged in place against the body passageway. As indicated above, the amount of force applied is at least that necessary to expand the stent (i.e. the applied the force exceeds the minimum force above which the stent material will undergo plastic deformation) while maintaining the patency of the body passageway. At this point, the balloon is deflated and withdrawn within the catheter, and is subsequently removed. Ideally, the stent will remain in place and maintain the target area of the body passageway substantially free of blockage (or narrowing).

See, for example, any of the following patents:
U.S. Pat. No. 4,733,665 (Palmaz),
U.S. Pat. No. 4,739,762 (Palmaz),
U.S. Pat. No. 4,800,882 (Gianturco),
U.S. Pat. No. 4,907,336 (Gianturco),
U.S. Pat. No. 5,035,706 (Gianturco et al.),
U.S. Pat. No. 5,037,392 (Hillstead),
U.S. Pat. No. 5,041,126 (Gianturco),
U.S. Pat. No. 5,102,417 (Palmaz),
U.S. Pat. No. 5,147,385 (Beck et al.),
U.S. Pat. No. 5,282,824 (Gianturco),
U.S. Pat. No. 5,316,023 (Palmaz et al.),
U.S. Pat. No. 5,755,771 (Penn et al.),
U.S. Pat. No. 5,906,640 (Penn et al.),
U.S. Pat. No. 6,217,608 (Penn et al.),
Canadian patent 1,239,755 (Wallsten), and
Canadian patent 1,245,527 (Gianturco et al.),
for a discussion on previous stent designs and deployment systems.

To date, most stent development has focused on the so-called coronary stents. While a number of advances in art of coronary stent development have been made, there is room for improvement.

One area which has received little or no attention is the area of endovascular treatment of aortic disease. At this point it is useful to review diseases of the aorta.

Aortic diseases contribute to the high overall cardiovascular mortality. Relatively new imaging modalities (e.g., transesophageal echocardiography, magnetic resonance tomography, helical computed tomography, and electron beam computed tomography) have been introduced during the last decade. These new imaging techniques facilitate better and/or earlier diagnosis of aortic diseases, even in emergency situations. These new imaging techniques have had an effect on patient management during recent years allowing more rapid diagnosis and decision making.

Figure 1:
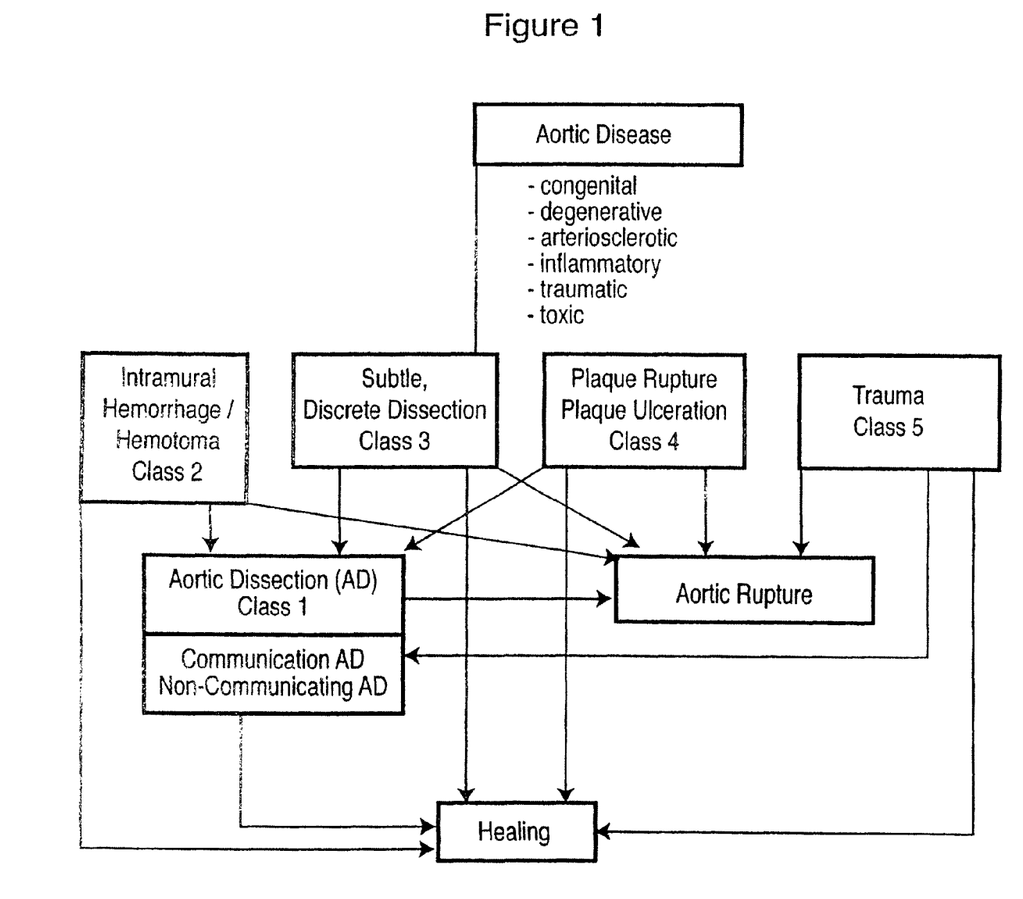
FIG. 1 illustrates a summary of the various categories of aortic disease.

Generally, aortic disease is caused by mechanisms which weaken the strength of the aortic wall, particularly, the aortic media. Such wall weakening leads to higher wall stress, which can induce aortic dilatation and aneurysm formation, eventually resulting in aortic dissection or rupture. The various categories of aortic disease are summarized in FIG. 1.

Diseases of the aorta are a significant problem in medicine. There are two general approaches: drug treatment and surgery. Drug treatment is used to lower blood pressure—this approach is disadvantageous since, at best, it modulates the effect of the disease while still leaving the patient at significant risk. Surgery is disadvantageous due to the high mortality and morbidity, even in centers of excellence. The increasing age of the population is resulting in an increased incidence of aortic disease as it is a degenerative disease. Further, aortic stiffness increases with age thereby reducing coronary and other artery perfusion.

There are three (3) indications of aortic disease which are regularly of clinical interest: (1) aortic dissection, (2) blunt chest trauma (with consequential trauma to the aorta), and (3) aortic sclerosis.

Aortic dissection is known to occur in approximately 15-20 cases/1 million inhabitants/year with a mortality of 50% in the first year and 5% per hour for the first 5 hours after the onset of symptoms. It results in a splitting of the aortic wall, a bleeding into the wall with formation of a true and false (new) lumen separated by a flap called "intima" with tear or "rupture point". In patients with involvement of the ascending aorta, surgery is performed and drug treatment preferred in patients with involvement of the descending aorta. As stated above, despite surgeries mortality is still high. The main problem is the organ perfusion of the abdomen which results in shock and multiorgan failure. Relatively recent studies have demonstrated that intramural hemorrhage, intramural hematoma, and aortic ulcer may be signs of evolving dissections or dissection subtypes. Currently, the various forms of dissection may be classified as follows:

Class 1 (FIG. 2a): Classical aortic dissection with an intimal flap between true and false lumen;

Class 2 (FIG. 2b): Medial disruption with formation of intramural hematoma/hemorrhage;

Class 3 (FIG. 2c): Discrete/subtle dissection without hematoma, eccentric bulge at tear site;

Class 4 (FIG. 2d): Plaque rupture leading to aortic ulceration, penetrating aortic atherosclerotic ulcer with surrounding hematoma, usually subadventitial; and Class 5 (FIG. 2e): Iatrogenic and traumatic dissection.

Each of these classes of dissection can be seen in their acute and chronic stages; chronic dissections are considered to be present if more than 14 days have elapsed since the acute event.

Figures 2A, 2B, 2C, 2D, 2E:
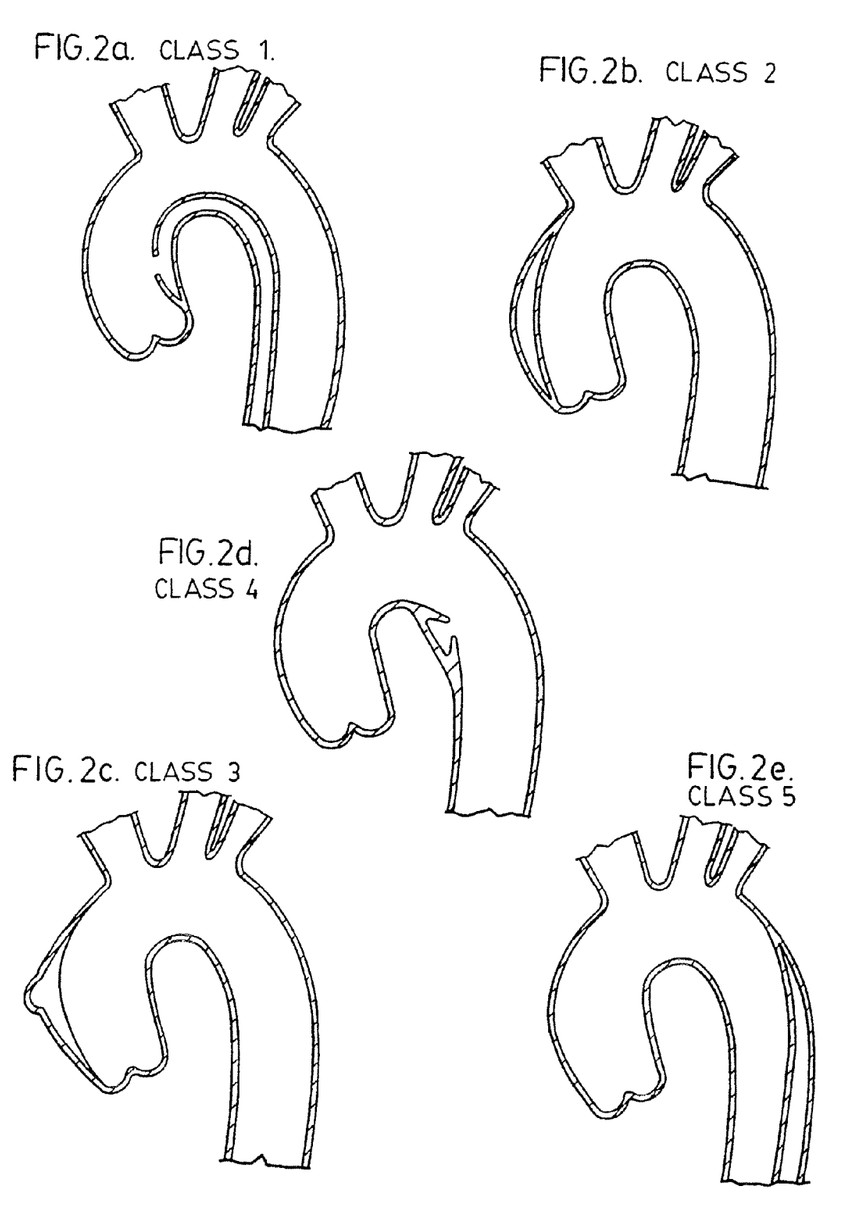
FIGS. 2a-2e illustrate various categories of dissection of the aorta.

Classic Aortic Dissection (Class 1—FIG. 2a)

Acute aortic dissection is characterized by the rapid development of an intimal flap separating a true lumen and false lumen. Due to the pressure difference the true lumen is usually smaller than the false lumen. Intimal flap tears characterize communicating dissections. However, tears are not always found and non-communicating dissections are not uncommon. The dissection can spread from diseased segments of the aortic wall in an antegrate or retrograde fashion, involving side branches and causing other complications.

Intramural Hematoma/Hemorrhage (Class 2—FIG. 2b)

An intramural hematoma is believed to be the initial lesion in the majority of cases of cystic medial degeneration leading to aortic dissection in which the intimal tear seems to be secondary to preceding intramural dissection. Intramural hematoma may be the result of ruptured normal-appearing vasa vasorum which are not supported by the surrounding aortic media or the result of rupture of diseased vasa vasorum. As a dissecting hematoma extends along the aorta the weakened inner wall is subjected to the elongating force of the diastolic recoil. Differences in elasticity between the aortic fibrous adventitia and the inner more elastic media may play an additional role.

In autopsy studies, dissecting aneurysms without tears have been found in up to 12% of 311 autopsies. Others studies have reported an incidence of 4% in 505 cases. In a series of sudden deaths, 67% of patients with dissections did not have tears. The incidence of intramural hemorrhage and hematoma in patients with suspected aortic dissection, as observed by various new imaging techniques, seems to be in the range of 10-30%.

There are two distinct types of intramural hematoma and hemorrhage.

Type I intramural hematoma and hemorrhage shows a smooth inner aortic lumen, the diameter is usually less than 3.5 cm, and the wall thickness greater than 0.5 cm. Echo free spaces (seen echocardiographically) as a sign of intramural hematoma are found in only .quadrature. of the patients. The mean longitudinal extent of the hematoma is about 11 cm and the echo free spaces show minimal or no signs of flow.

Type 11 intramural hematoma and hemorrhage occurs in aortic arteriosclerosis. A rough inner aortic surface with severe aortic sclerosis is characteristic, the aorta is dilated to more than 3.5 cm, and calcium deposits are frequently found. Mean wall thickness is 1.3 cm with a range of from about 0.6 to about 4 cm, and echo free spaces are found in 70 degrees of the patients studied. The longitudinal extension has a similar range as in Type I hematoma, usually about 11 cm. Intramural hemorrhages are more often found in the descending than in the ascending aorta.

The fact that intramural hemorrhage and hematoma can lead to aortic dissection has only be demonstrated in follow-up studies. Acute aortic dissection as a consequence of intramural hemorrhage and hematoma develops in from about 28% to about 47% of the patients. It is associated with aortic rupture in from about 21% to about 47%; and regression is seen in about 10% of the patients.

Subtle-Discrete Aortic Dissection (Class 3—FIG. 2c)

The structural weakness can either lead to clinically undetected disease or minor forms of aortic dissection. Subtle dissection has been described as a partial stellate or linear tear of the vessel wall, covered by thrombus. After the partial tear forms a scar, this constellation is called abortive, discrete dissection. Partial ruptures of the inner layer of the aorta allow the blood to enter the already damaged media and thus cause dissection of the aortic wall, eventually leading to a second lumen within the wall, to a rupture or healing during follow-up.

Plague Rupture/Ulceration (Class 4—FIG. 2d)

Ulceration of atherosclerotic aortic plaques can lead to aortic dissection or aortic perforation. This was first observed by computed tomography. Innovations in imaging techniques (e.g., intravascular ultrasound, spiral computed tomography and magnetic resonance imaging) provide new insight. The ability to diagnose aortic ulceration has thereby been improved and further affects the descending thoracic aorta, as well as the abdominal aorta, and is usually not associated with an extensive longitudinal propagation or branch vessel compromise. Valvular, pericardial, or other vascular complications seem to be rare. The ulcer may penetrate beyond the internal border, often with an nipple-like projection with subjacent Type II intramural hematoma formation. The continuous erosion of the atherosclerotic plaque may eventually violate the internal elastic membrane. False aneurysms, aortic rupture or dissections may occur.

Aortic sclerosis is normally divided into four grades from thickening of the intima (Grade I) up to the development of free floating thrombi (Grade IV) with the danger of embolism. In elderly patients, the incidence of the Grade IV aortic sclerosis is increasing. This has lead to a significant occurrence of stroke in patients. Thus, if a treatment of aortic sclerosis Grade IV with thrombi free floating in the aortic lumen could be developed, this would likely obviate or mitigate the consequential occurrence of stroke.

Currently, there is no reliable treatment approach for aortic sclerosis particularly the Grade IV type. Anticoagulation is a known approach, however this treatment must be accepted with the danger of hemorrhagic strokes, particularly in the older patients Further, the therapy is very difficult to monitor. Surgery is very complicated and has a high mortality and morbidity. Currently, surgery is not seen as a desirable alternative to anticoagulation therapy.

Traumatic/Iatrogenic Aortic Dissection (Class 5—FIG. 2e)

Blunt chest trauma usually causes dissection of the ascending aorta and/or the region of the ligamentum Botalli at the aortic isthmus. Iatrogenic dissection of the aorta may rarely occur during heart catheterization. It is regularly seen following angioplasty of an aortic coarctation, but can also be observed after cross clamping of the aorta and after the use of intraaortic balloon pumping. Most catheter-induced dissections are retrograde dissections. They will usually decrease in size as the false lumen thromboses. Proximal progression of the coronary dissection into the aortic root may be observed. In blunt chest trauma, the large acceleration of the aorta is leading to an intimal, medial or transsection of the aorta particularly at the adjunction at the aortic arch and the descending aorta (15-20% of blunt chest trauma cases are related to aortic injury). As a consequence of this blunt chest trauma, mediastinal hematoma can occur with abrupt death of the patient. The blunt chest trauma is known to occur in accidents involving heavy motorcycles and cars, as well as in other chest traumas. The diagnosis is verge difficult but has been improved by transesophageal echocardiography. Typically, the damage to the aorta is limited to a small portion comprising 3 cm-5 cm of the aorta. Conventionally, surgery was the only treatment to stabilize these patients. A mortality rate of 90% has been seen if surgery was not timely preformed. Even if surgery was timely performed, there is a significant mortality rate.

Most prior art attempts to improve surgical techniques to treat aortic dissection have not be particularly successful.

It is also worth pointing out that the so-call "stent grafts" are not well suited for treating diseases of the aorta. Specifically, a conventional stent graft is generally of a fixed longitudinal length. Since the anatomy of each patient is different and the overall longitudinal length of the aortic or other endoluminal disease condition is variable, the stent graft should be of a specific or customized longitudinal length so as to minimize the occurrence side branch blockage. This is inconvenient and requires inventory stocking of a number of stent grafts having a variety of different longitudinal lengths to have devices on hand for use in most situations.

Thus, despite the advances made in the art, there is still a need for an endovascular prosthesis capable obviates or mitigates at least one of the above-mentioned disadvantages of the prior art. Specifically it would be desirable to have an endovascular prosthesis whose longitudinal length could be adjusted in vivo by the physician during implanted of the prosthesis.

DISCLOSURE OF THE INVENTION

It is an object of the present invention to provide a novel endovascular prosthesis which obviates or mitigates at least one of the above-mentioned disadvantages of the prior art.

Accordingly, in one of its aspects, the present invention provides an endovascular prosthesis for implantation in a body passageway, the prosthesis comprising a tubular wall, the tubular wall being: (i) movable between a first longitudinal length and a second longitudinally length, and (ii) radially expandable for implantation of the prosthesis in the body passageway.

In another of its aspects, the present invention provides an endovascular prosthesis for implantation in a boded passageway, the prosthesis comprising a first tubular wall and a second tubular wall in longitudinal sliding engagement with one another, the first tubular wall and the second tubular wall being radially expandable for implantation of the prosthesis in the body passageway.

In another of its aspects, the present invention provides a method for endovascular blocking of an endovascular disease condition located between a first location point and a second location point in a target body passageway of a patient with an endovascular prosthesis comprising a first tubular wall and a second tubular wall in longitudinal sliding engagement with one another the first tubular wall and the second tubular wall being radially expandable, the method comprising the steps of:

inserting the prosthesis and a catheter within a body passageway by catheterization of the body passageway;
translating the prosthesis and catheter to a target body passageway in which the endovascular disease condition is located;
positioning the distal end of the prosthesis such the distal end of the prosthesis is substantially aligned with the first location point;
extending the distal end of the prosthesis with respect to the catheter;
exerting a radially outward expansive force on the distal end of the tubular wall such that the distal end of the tubular wall is urged against the target body passageway;
fixing a proximal portion of the prosthesis with respect to the catheter;
retracting the catheter thereby longitudinally extending the expansible portion of the tubular wall until the proximal end of the prosthesis is substantially is substantially aligned with the second location point;
freeing the prosthesis with respect to the catheter;
retracting the catheter to expose the proximal end of the endovascular prosthesis; and
exerting a radially outward expansive force on the proximal end of the tubular wall such that the proximal end of the tubular wall is urged against the target body passageway.

In yet another of its aspects, the present invention provides a method for endovascular blocking of an endovascular disease condition located between a first location point and a second location point in a body passageway of a patient with endovascular prosthesis comprising a tubular wall comprising a distal end and a proximal end, the tubular wall being: (i) movable between a first longitudinal length and a second longitudinally length, and (ii) radially expandable for implantation of the prosthesis in the body passageway, the method comprising the steps of:

disposing the prosthesis in a catheter;
inserting the prosthesis and catheter within a body passageway by catheterization of the body passageway;
translating the prosthesis and catheter to a target body passageway in which the endovascular disease condition is located;
extending the distal end of the prosthesis from the catheter,
positioning the distal end of the prosthesis such the distal end of the prosthesis is substantially aligned with the first location point;
exerting a radially outward expansive force on the distal end of the tubular wall such that the distal end of the tubular wall is urged against the target body passageway;
urging the proximal end of the prosthesis against the catheter;
retracting the catheter thereby longitudinally extending the expansible portion of the tubular wall until the proximal end of the prosthesis is substantially is substantially aligned with the second location point;
freeing the proximal end of the prosthesis with respect to the catheter;
retracting the catheter to expose the proximal end of the endovascular prosthesis; and
exerting a radially outboard expansive force oil the proximal end of the tubular wall such that the proximal end of the tubular wall is urged against the target body passageway.

Generally, the present prosthesis can be advantageously used to treat the indications of aortic disease referred to hereinabove. Specifically, as will be described in more detail hereinbelow, the present endovascular prosthesis has a longitudinal length which may be varied in vivo to optimize the length there while obviating or mitigated side branch occlusion.

Thus, the preferred form of the present endovascular prosthesis device is a stent system which comprises a longitudinally expansible or variable portion. Preferably, the longitudinally expansible or variable portion is, at least partially radially, covered by a non-porous or graft material. Preferably, the non porous section extends longitudinally a distance in the range of from about 2 cm to about 10 cm, more preferably from about 3 cm to about 8 cm, even more preferably from about 3 cm about 6 cm.

With reference to aortic dissection, the present prosthesis normally will be implanted at the side of the intima tear in order to block the flow from the true lumen into the false lumen at the dissection connection. The present prosthesis may be advantageously used in optimizing the length of the prosthesis in treating dissection of the descending part of the aorta.

A preferred feature of the present endovascular prosthesis is that it has only a partial, radial non-porous or graft covering. Placement and positioning of the device can be facilitated by intravascular ultrasound and transesophageal echocardiography blocking the tear and while obviating or mitigating covering the entire aortic wall—e.g., the portion of the aortic wall possibly containing important side branches.

Once implanted, an advantage of the preferred form of the present endovascular prosthesis is that it allows flow from the proximal to the distal aorta even during the implantation of the device due to the unique design. In contrast, conventional stent grafts must be used with the concurrent danger of abrupt rise of blood pressure leading to an extension and enlargement of the dissection.

The present endovascular prosthesis may be used advantageously to block the tear, thereby obviating or mitigating flow from the true lumen to the false lumen. Thus, the healing process begins which, in the successful cases, will lead during follow-up within 6 months to total obliteration of the false lumen and strengthening of the aortic wall. In addition the pressure in the false lumen is reduced or eliminated and thereby, the true lumen can expand and improve the organ perfusion.

When properly deployed, the present endovascular prosthesis will protect the diseased pant of the aorta, so that little or no blood is escapes from the lumen to the mediastinum and thereby, the patient is stabilized. Using intravascular ultrasound and transesophageal echocardiography, the present endovascular prosthesis may be appropriately navigated to block the damage of the aorta. Again as in treatment of aortic dissection, it is important to avoid blockage of multiple arteries which are supplying the back bone since this can lead to paraplegia with enormous consequences for the patient.

Indeed, to the knowledge of the present inventors, the present endovascular device is the first such device to be useful in reliable treatment of aortic diseases. Thus, with the present endovascular device, blockage of the aortic flow is obviated or mitigated and abrupt blood pressure increases (which could lead to a fatal event) are avoided. Further, since the present device may be deployed endovascularly (i.e. non-surgically), it is generally safer for the patient and is less of a burden on public health systems.

The present endovascular prosthesis may be used advantageously to wrap the intimal flaps and thrombi to the aortic wall and thereby obviate or mitigate the danger of stroke and emboli without the need for anticoagulation. As the preferred form of the present prosthesis covers only a radial portion of the aortic circumference, blocking of side arteries, which are supplying the back bone, is obviated or mitigated. As the preferred form of the present prosthesis is open and not blocking the flow from the proximal and distal aorta during the implantation, a blood pressure increase is obviated or mitigated. Thus, a unique advantage of the present prosthesis is that it can be used even in multiple places of the aorta when more parts of the aorta are showing thrombus formation.

BRIEF DESCRIPTION OF THE DRAWINGS

Embodiments of the present invention will be described with reference to the accompanying drawings, in which.

BEST MODE FOR CARRYING OUT THE INVENTION

Figure 3:
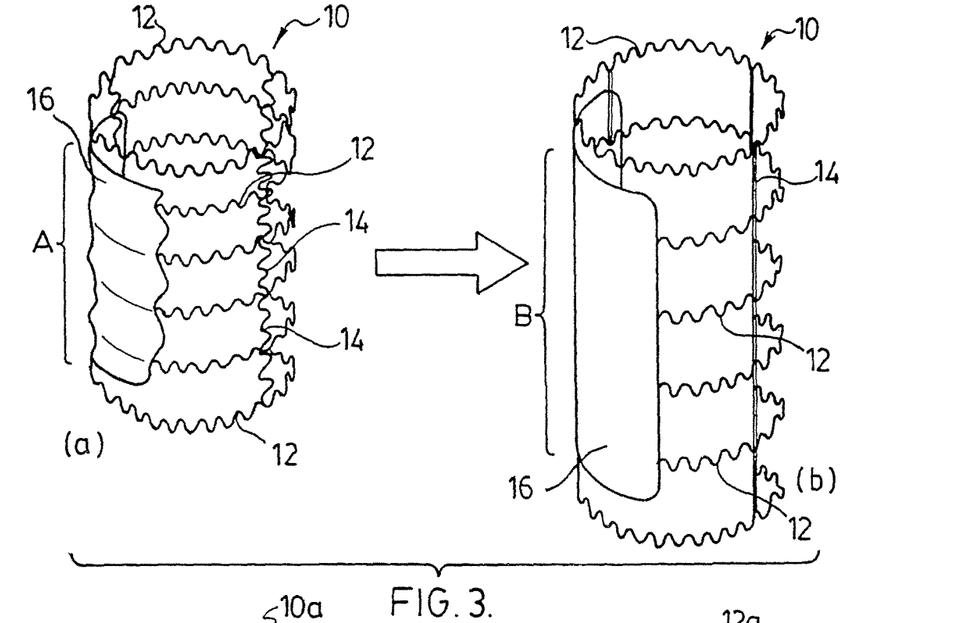
FIGS. 3a-3b illustrates a perspective view of an expandable prosthesis in accordance with the present invention in its retracted and extended position.

Thus, with reference to FIG. 3, there is illustrated an expandable prosthesis 10 which comprises a plurality of annular members 12 which are joined to one another by one or more longitudinal spines 14. Annular members 12 are radially expandable. Further, spine 14 is longitudinally expandable. As disclosed in U.S. Pat. No. 6,217,608 (referred to above and incorporated herein by reference in the last paragraph of the specification), annular members 12 and spines 14 comprise S-shaped members which are expandable.

Disposed over a portion of expandable prosthesis 10 is a cover material 16. Cover material 16 is adhered to various of annular members 12.

In the longitudinally retracted version of endovascular prosthesis 10 (i.e. FIG. 3a), the longitudinal length of cover material 16 is greater than the longitudinal length A of endovascular prosthesis 10 over which it is disposed. This can be achieved by a suitable means such as folding of cover material 10 and the like. Alternatively, cover materials 16 can be made of a material which can stretch.

As shown in FIG. 3b, it is possible to lengthen endovascular prosthesis 10 prior to radial expansion thereof. The manner by which this is achieved will be described hereinbelow. The point is, as the spacing between adjacent annular members 12 is increased, cover material 16 unfolds or otherwise lengthens (e.g., by stretching) to allow the longitudinal length B of cover material 16 to increase compared to length A in FIG. 3a.

Figure 4:
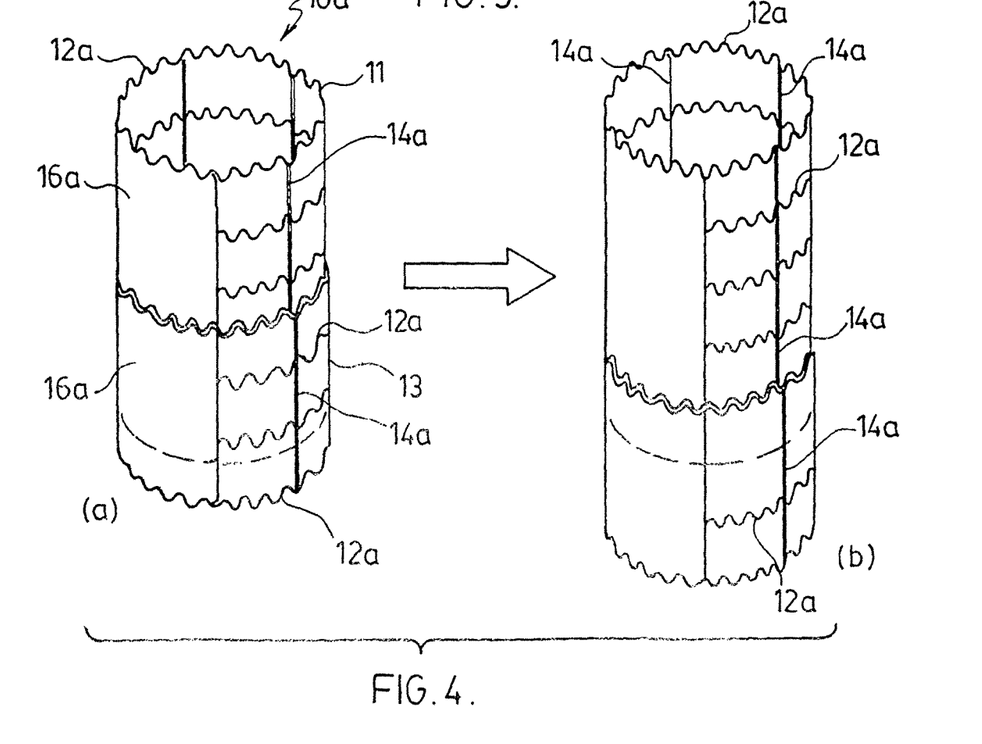
FIGS. 4a-4b illustrates a perspective view of an alternate embodiment of the present endovascular prosthesis in the retracted and extended position.

An alternate embodiment is illustrated in FIG. 4. Specifically, there is illustrated an endovascular prosthesis 10a comprising a first section 11 and a second section 13. Sections 11 and 13 are longitudinally movable with respect to each other (e.g., in a telescoping manner). Each of sections 11 and 13 are similarly constructed in that each comprises a series of annular members 12a which are interconnected by a longitudinal spine 14a.

In the embodiment illustrated in FIG. 4, lengthening of endovascular prosthesis 10a is achieved by relative of extension of section 11 with respect to section 13. This enlarges the overall length of cover material 16a which is disposed on each of sections 11 and 13.

As will be appreciated by those of skill in the art, the combination of annular members 12 and 14 (FIG. 3) and sections 11 and 13 (FIG. 4) may be any conventional stent design which is preferably optimized to facilitate navigation of the prosthesis to the target site in the anatomy. The preferred design for the stent sections is that disclosed in the Penn et al. International patent applications referred to above. Of course, those of skill in the art will recognize that the present endovascular prosthesis is not restricted to the use of the specific stent designs illustrated in FIGS. 3 and 4, and that any generally skill stent design may be used.

Preferably, cover material 16 (FIG. 3) and 16*a* (FIG. 4) is a sheet material such as Dacron™, Gortex™, other polymeric materials, bovine pericardium and the like. The nature of the material used for this purpose is not particularly restricted. It is preferred that the material be substantially impermeable to bodily fluids, that it is generally biocompatible and that the physical nature thereof does not impede delivery, deployment or general efficacy of the endovascular prosthesis after it has been implanted.

Cover material 16 (FIG. 3) and 16*a* (FIG. 4) may also be derived from a silicone-based material such as those commercially available from NuSil Technology (Carpenteria, Calif.). A non-limiting example of such material is derived from a silicone-based dispersion commercially available from NuSil Technology under trade name MED-6640. This material is usually obtained as a liquid dispersion in an organic insolvent such as xylene. The dispersion may be used as such or the viscosity thereof bay he altered as desired by addition of further solvent.

Preferably, the cover material is attached to an otherwise tubular stent structure. The means by which attachment may be achieved is not particularly restricted. For example, the cover material could be fixed to the appropriate spot on the stent using a suitable adhesive. Alternatively, the cover material could be sewn onto the stent. Those of skill in the art will conceive of a number of other means by which the cover material may be fixed to the stent structure.

In another embodiment, cover material 16 (FIG. 3) and 16*a* (FIG. 4) may be made of the same material as the remainder of prosthesis 10 (FIG. 3) and 10*a* (FIG. 4) but preferably suitably modified to comprises a number of slits, microcuts, slots, apertures or the like to reconcile the feature of impeding bodily fluid (e.g., blood) therethrough with the feature of rendering the cover material sufficiently flexible so as to permit delivery and deployment of the expandable prosthesis.

With reference FIGS. 5-16, a preferred mode of deploying endovascular prosthesis 10*a* will be illustrated. For sake of illustration only, various of the structural details of endovascular prosthesis 10*a* discussed above are omitted from FIGS. 5-16. Further, for illustrative purposes only, endovascular prosthesis 10*a* shown in FIGS. 5-16 is constructed from a plastically deformable material such as stainless steel, tantalum, or the like. The plastically deformable material may comprise a laminar structure. The laminar structure may comprise a layer of plastically deformable material and a layer of radioopaque material.

Figure 5:
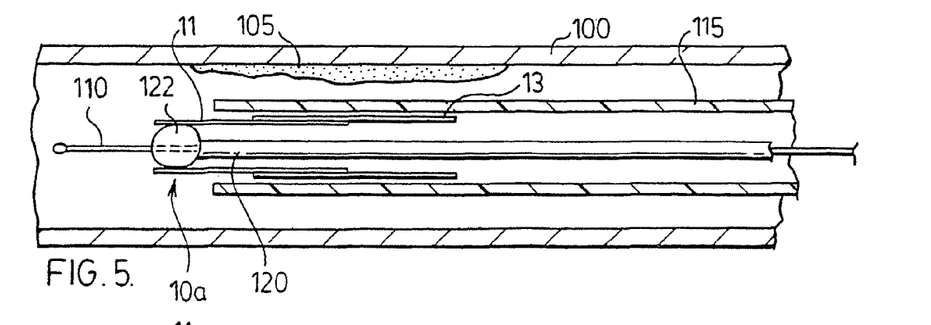
FIGS. 5-15 illustrate a sectional view of deployment of an embodiment of the present endovascular prosthesis in a lumen.

Thus, with reference to FIG. 5, there is illustrated a lumen 100 (this could be the ascending aorta referred to in FIG. 2 above) having a blockage 105 disposed on a wall thereof. In accordance with conventional catheterization techniques, initial steps (not illustrated for clarity) involve disposing a guidewire 110 in lumen 100 such that the distal end of guidewire 10 is distal blockage 105. Thereafter, a guiding catheter 115 is disposed in a manner such that the distal end of guide catheter 115 is proximal the distal extremity of blockage 105.

Thereafter, endovascular prosthesis 10*a* disposed on a balloon catheter 120, (or other suitable delivery system), preferably comprising an elastomeric balloon at the distal end thereof, is extended from guiding catheter 115 to expose distal portion of section 11 of endovascular prosthesis 10*a*.

Figure 6:
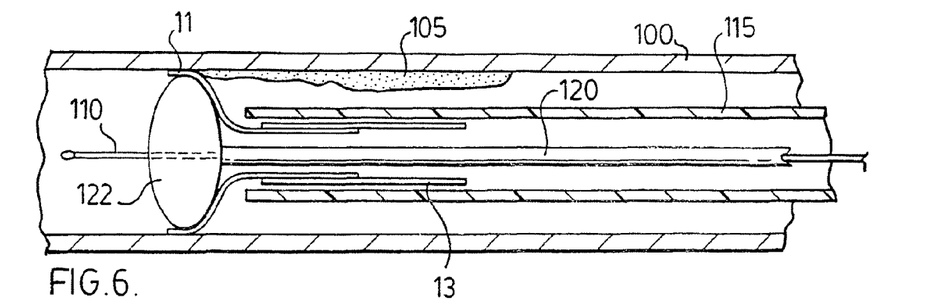

Thereafter, a balloon 122 disposed on the distal end of balloon catheter 120 is expanded in a conventional manner. This urges the distal end of section 11 of endovascular prosthesis 10*a* against lumen 100 as shown in FIG. 6.

Figure 7:
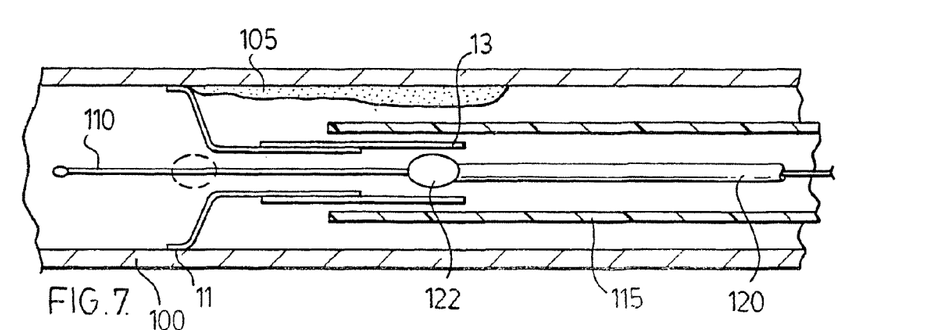
Figure 8:
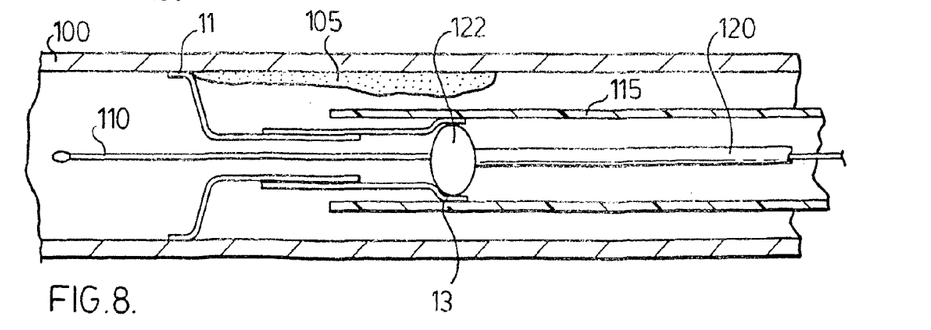

Next, balloon 122 is deflated and balloon catheter 120 is retracted such that balloon 122 is near the proximal end of section 13 of endovascular prosthesis 10*a*—this is shown in FIG. 7.

Thereafter, balloon 122 is partially expanded to urge the proximal end of section 13 of expandable prosthesis 10*a* against the inside of guiding catheter 115—this is shown in FIG. 5.

Figure 9:
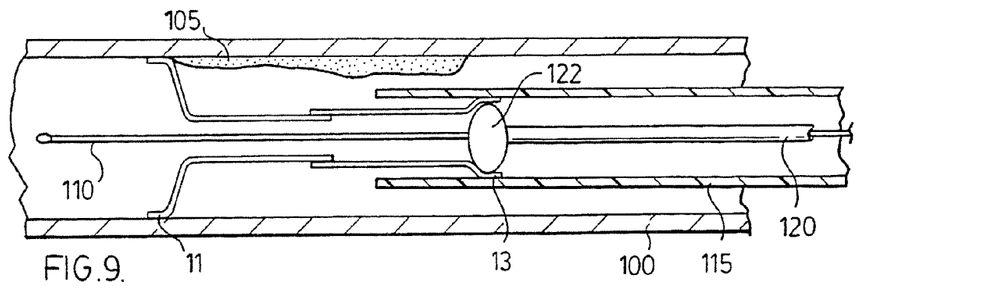

Next, guiding catheter 115 is retracted as shown in FIG. 9. Since the proximal end of section 13 of endovascular prosthesis 10*a* is urged against the inside of guiding catheter 115 during this step, this effectively results in relative extension of section 13 from section 11 of endovascular prosthesis 10*a*.

Figure 10:
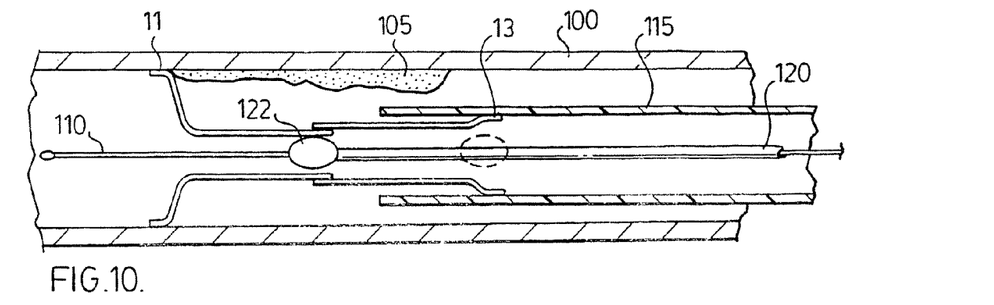

Next, balloon 122 of balloon catheter 120 is deflated and balloon catheter 120 is repositioned such that balloon 122 is near the overlapping region of sections 11 and 13 of endovascular prosthesis 10*a*—see FIG. 10.

Figure 11:
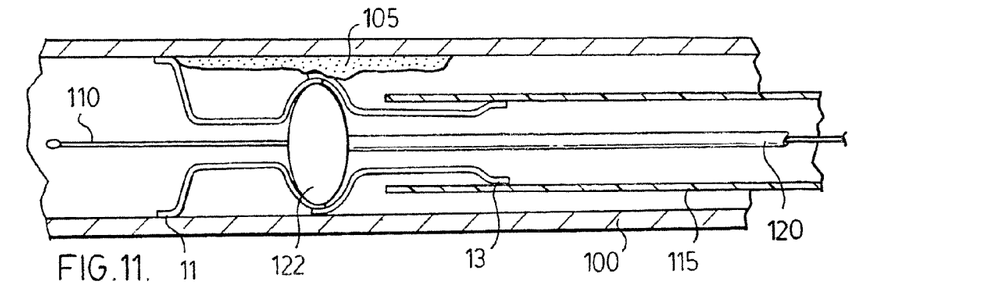

At this point, balloon 122 is expanded which results in urging of sections 11 and 13 of endovascular prosthesis 10*a* against lumen 100 as shown in FIG. 11.

Figure 12:
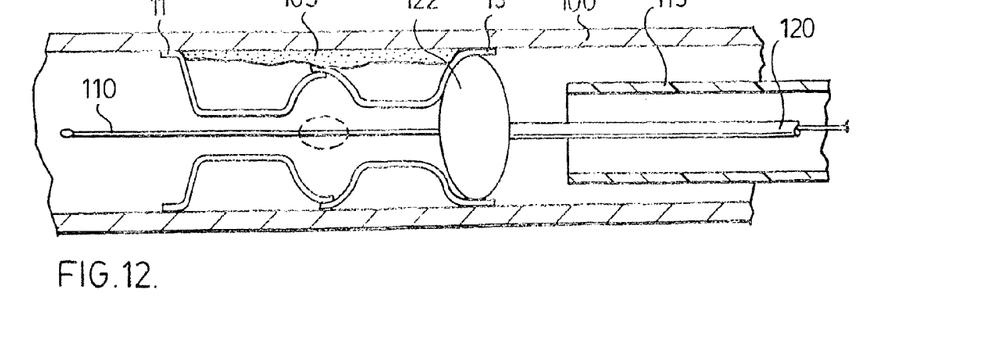

Thereafter, guiding catheter 115 is retracted to expose the entire expandable prosthesis 10*a* as shown in FIG. 12 and balloon 122 of balloon catheter 120 is repositioned to expand the proximal end of section 13 against lumen 100.

Figure 13:
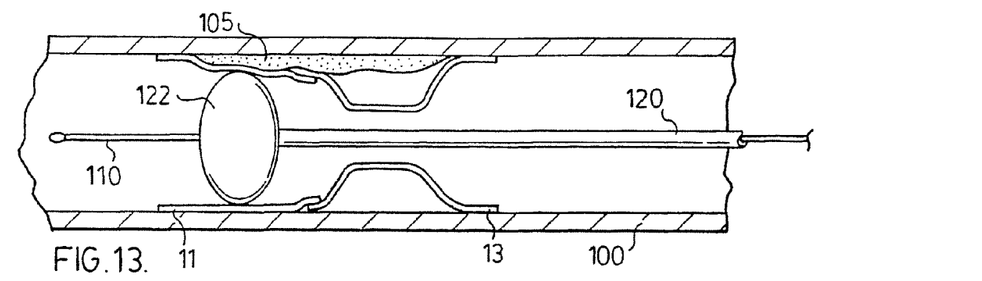
Figure 14:
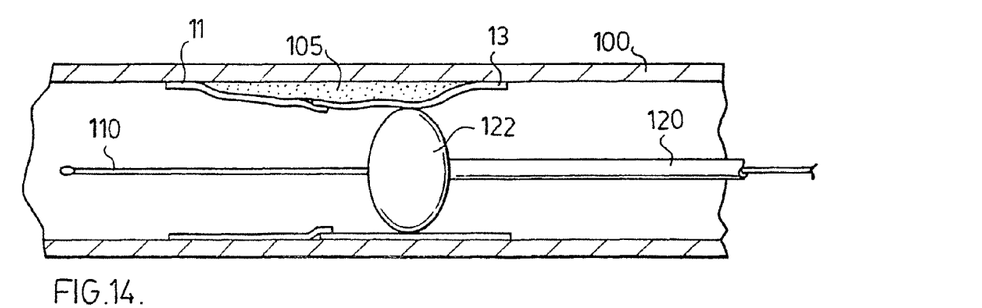
Figure 15:
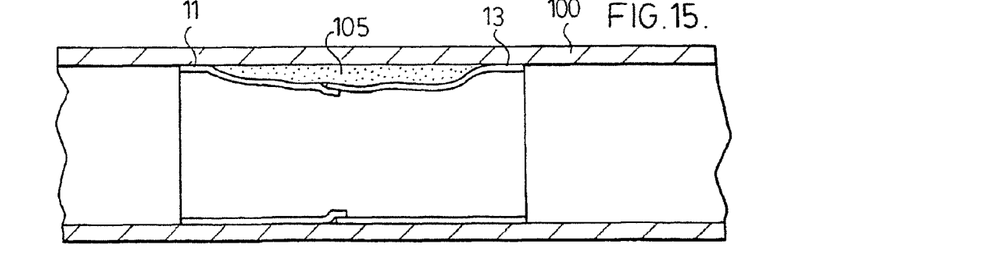

FIGS. 13 and 14 illustrates successive expansion steps along the length of endovascular prosthesis 10*a* with the result that it is "remodeled" to occlude blockage 105.

Of course, while not specifically illustrated, it is preferred that cover material 16*a* (FIG. 4) is positioned such that it occludes blockage 105.

Figures 16, 17:
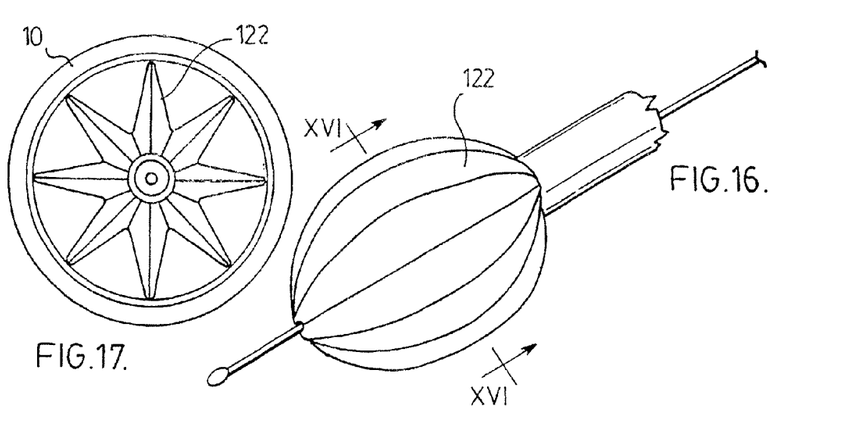
FIG. 16 illustrates a perspective view of a perfusion balloon useful in the embodiment illustrated in FIGS. 5-16.
FIG. 17 is a sectional view taken along line XVI-XVI in FIG. 16, as used in a body passageway.

FIGS. 16 and 17 illustrate a preferred perfusion balloon which is useful in the embodiment illustrated in FIGS. 5-15. The perfusion balloon is particularly useful to permit continued blood flow through lumen 100 during "remodeling steps" illustrated in FIGS. 12-14.

With reference to FIGS. 18-24, deployment of an alternate embodiment of the present endovascular prosthesis will be described. As will be evident to those of skill in the art, FIGS. 18-24 illustrate deployment of endovascular prosthesis in the ascending aorta of a patient. For clarity, the endovascular prosthesis is shown schematically as a series of hoops. Preferably, these hoops would be effectively interconnected by a covering material such that the longitudinal length of the prosthesis is adjustable by an accordion-type movement. Further, the specific aortic disease being treated is not shown, again for the purposes of clarity only.

Figures 18, 20:
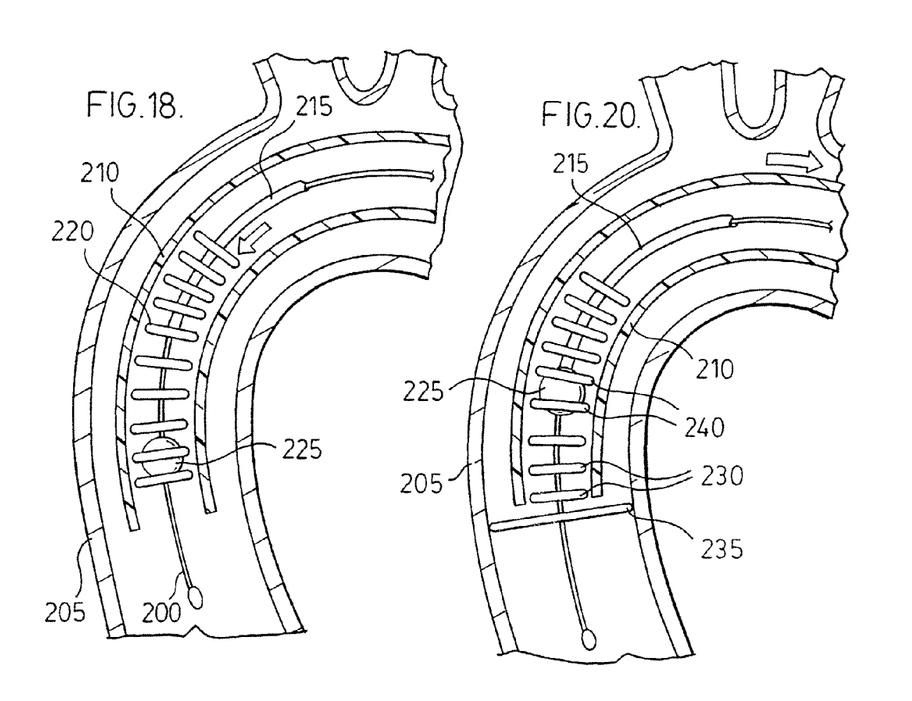
FIGS. 18-24 illustrate a sectional view of deployment of an alternate embodiment of a present endovascular prosthesis.

Thus, a guidewire 200 is navigated endovascularly to a region of the ascending aorta 205 just proximal the patient's heart (not shown). Thereafter, a combination of a sheath 210, a balloon catheter 215, and an endovascular prosthesis 220 is delivered over guidewire 200 to ascending aorta 205.

A balloon 225 disposed at the distal end of balloon catheter 215 is expanded slightly so as to be urged against a pair of hoops 230 just proximal a distal hoop 235 of prosthesis 220. Next, the combination of sheath 210 and balloon catheter 215 are retracted slightly in the direction of the arrow shown in FIG. 19. This exposes distal hoop 235 from sheath 210 resulting in self-expansion of distal hoop 235. Specifically, it is preferred that the hoops comprised in endovascular prosthesis 220 are constructed from a shape memory alloy such as Nitinol or the like.

Figure 19:
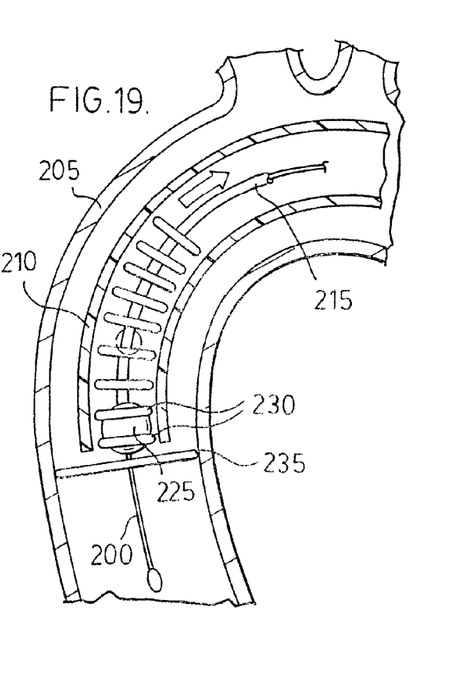

With reference to FIGS. 19 and 20, balloon 225 of catheter 215 is deflated, catheter 215 is retracted and balloon 225 is re-inflated so as to be urged against a pair of intermediately disposed hoops 240—see FIG. 20 for the repositioning of balloon 225 of catheter 215.

Figure 21:
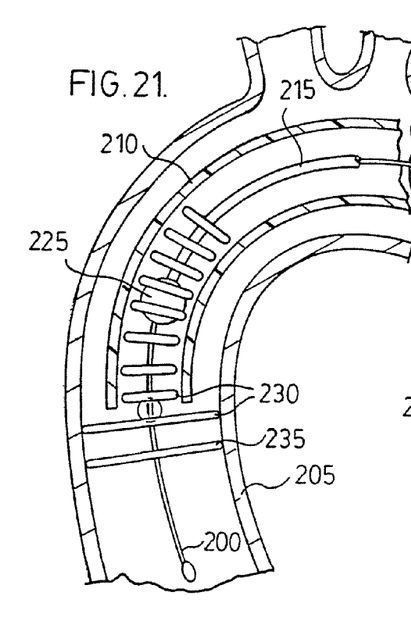
Figure 22:
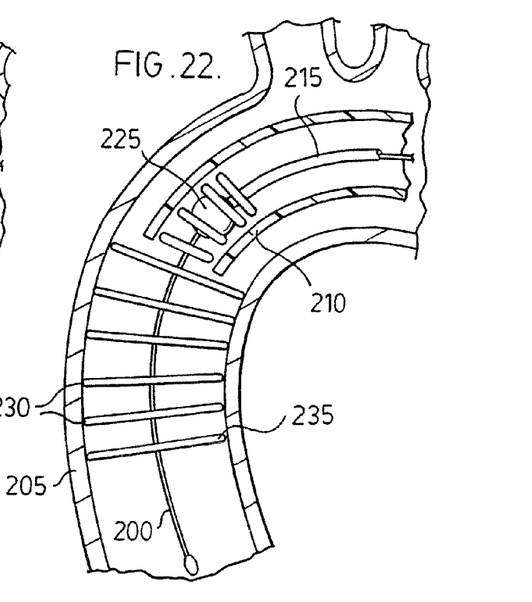
Figure 23:
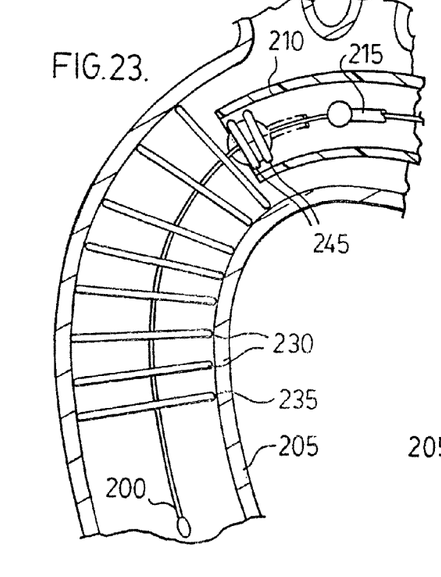

Next, the combination of sheath 210 and balloon catheter 215 is retracted in the direction of the arrow shown in FIG. 20. This results in exposure of successive hoops of endovascular prosthesis 220 as shown in FIG. 21. As more hoops of endovascular prosthesis 220 are exposed from sheath 210, it may be desirable to reposition balloon 225 of catheter 215 as shown in FIG. 22. The repositioning of balloon 225 of catheter 215 may be achieved as described above with reference to FIGS. 19 and 20.

Figure 24:
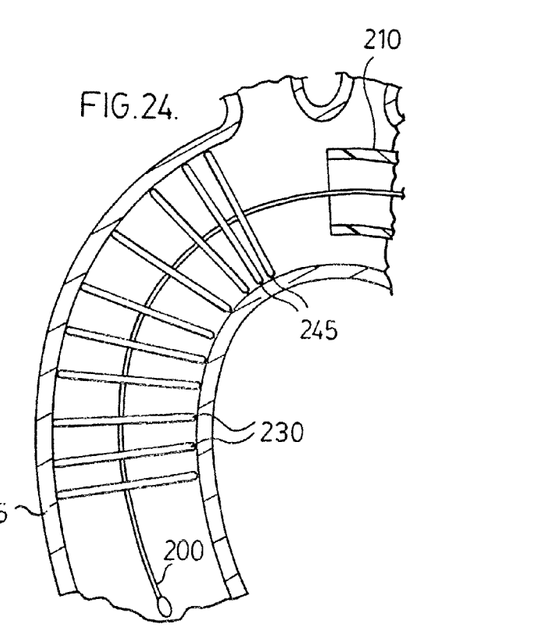
Figure 25:
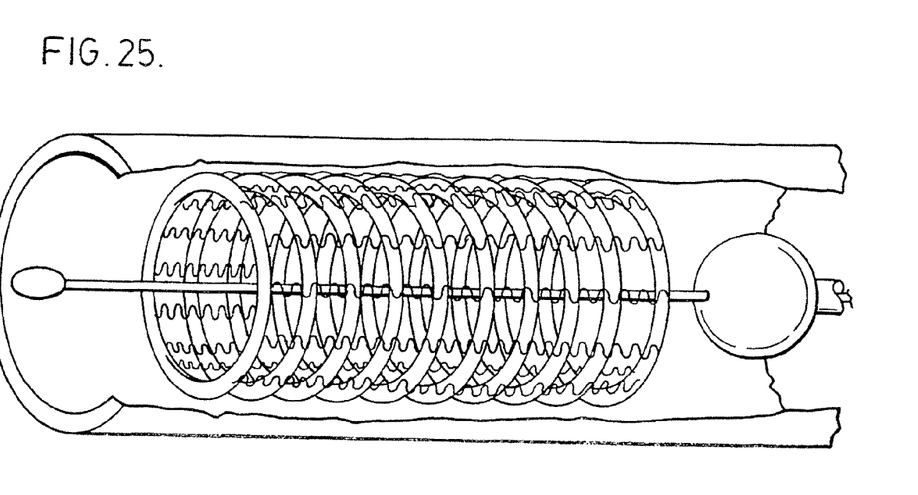
FIG. 25 illustrates a perspective view the endovascular prosthesis of FIGS. 18-24 after deployment.

Continued retraction of the combination of sheath 210 and balloon catheter 215 results in further hoops of endovascular prosthesis 220 being exposed from sheath 210 as shown in FIG. 22. With reference to FIG. 22, once the appropriate longitudinal length of endovascular prosthesis 220 has been reached, balloon 225 of catheter 215 is deflated and the combination of sheath 210 and balloon catheter 215 is retracted as shown in FIG. 24 thereby exposing a pair of proximally disposed hoops 245 of endovascular prosthesis 220. Thus, in the illustrated embodiment (FIG. 24), there is no substantial lengthening of the distance between proximally disposed hoops 245 of endovascular prosthesis 220. Thus, those who have skill in the art, will recognize that endovascular prosthesis 220 is particularly advantageous since the longitudinal length thereof mall be readily varied during implantation thereof in the patient. This is particularly advantageous where the target anatomy of the patient is subject to varying dimensions on a patient-by-patient basis. Further, the approach illustrated in FIGS. 18-24 is particularly advantageous since endovascular prosthesis 220 may be deployed while maintaining perfusion through the delivery system. Further, the present endovascular prosthesis is advantageous since, during delivery thereof, undesirable stretching and related stress to the aorta is minimized or avoided. By avoiding such stretching of the aorta, placement of the prosthesis can be more easily reconciled with pre-procedure measurements which are taken to determine the appropriate length and size of the vessel.

The present endovascular prosthesis may further comprise a coating material thereon. The coating material may be disposed continuously or discontinuously on the surface of the prosthesis. Further, the coating may be disposed on the interior and/or the exterior surface(s) of the prosthesis. The coating material can be one or more of a biologically inert material (e.g., to reduce the thrombogenicity of the prosthesis), a medicinal composition which leaches into the wall of the body passageway after implantation (e.g., to provide anticoagulant action, to deliver a pharmaceutical to the body passageway and the like) and the like.

The present endovascular prosthesis is preferably provided with a biocompatible coating in order to minimize adverse interaction with the walls of the body vessel and/or with the liquid, usually blood flowing through the vessel. The coating is preferably a polymeric material, which is generally provided by applying to the prosthesis a solution or dispersion of preformed polymer in a solvent and removing the solvent. Non-polymeric coating material may alternatively be used. Suitable coating materials, for instance polymers, may be polytetraflouroethylene or silicone rubbers, or polyurethanes which are known to be biocompatible. Preferably, however, the polymer has zwitterionic pendant groups, generally ammonium phosphate ester groups, for instance phosphoryl choline groups or analogues thereof. Examples of suitable polymers are described in International Publication Numbers WO 93/16479 and WO 93/15775. Polymers described in those specifications are hemo-compatible as well as generally biocompatible and, in addition, are lubricious. It is important to ensure that the surfaces of the prosthesis are completely coated in order to minimize unfavorable interactions, for instance with blood, which might lead to thrombosis in the parent vessel.

This good coating can be achieved by suitable selection of coating conditions, such as coating solution viscosity, coating technique and/or solvent removal step.

While this invention has been described with reference to illustrative embodiments and examples, the description is not intended to be construed in a limiting sense. Thus, various modifications of the illustrative embodiments, as well as other embodiments of the invention, will be apparent to persons skilled in the art upon reference to this description. For example, those of skill in the art will appreciate that it is possible to modify the specific embodiment illustrated in FIGS. 3 and 4 such (i.e., a partially covered endovascular prosthesis) that the prosthesis is completely cover or completely uncovered. Further, in the event the prosthesis is partially or completely covered, it is possible to utilize a bioadhesive or the like to promote sealing engagement of the coveted portion of the prosthesis and the section of the body passageway against which it is urged. It is therefore contemplated that the appended clams still cover any such modifications or embodiments.

All publications, patents, and patent applications referred to herein are incorporated by reference in their entirety to the same extent as if each individual publication, patent or patent application was specifically and individually indicated to be incorporated bag reference in its entirety.

What is claimed is:

1. An unexpanded ex vivo endovascular prosthesis for implantation in a body passageway, the prosthesis comprising:
   a unitary tubular wall, the tubular wall, prior to implantation into the body passageway, being independently:
   (i) movable between a first longitudinal length and a second longitudinal length without changing the diameter of the unitary tubular wall;
   (ii) radially expandable for implantation of the prosthesis in the body passageway;
   the unitary tubular wall comprising two adjacent undulating circumferential members coupled together by two adjacent undulating longitudinal members;
   a covering material coupled to said two adjacent undulating circumferential members;
   said two adjacent undulating longitudinal members being longitudinally expandable prior to radial expansion of said two adjacent undulating circumferential members; and
   said covering material having a longitudinal length that is greater than a longitudinal length between two adjacent undulating circumferential members prior to the longitudinal expansion of said two adjacent undulating circumferential members.

2. The endovascular prosthesis defined in claim 1, wherein the tubular wall comprises an annular portion for occlusion of a section of the body passageway, the annular portion comprising a first porous section and a non-porous section.

3. The endovascular prosthesis defined in claim 2, wherein the tubular wall comprises a second porous section adjacent the annular portion.

4. The endovascular prosthesis defined in claim 3, wherein the tubular wall comprises a third porous section adjacent the annular portion.

5. The endovascular prosthesis defined in claim 2, wherein the annular portion spans 360 degrees of the tubular wall, and wherein the non-porous section radially spans from about 90° to about 270° of the annular portion.

6. The endovascular prosthesis defined in claim 2, wherein the annular portion spans 360 degrees of the tubular wall, and wherein the non-porous section radially spans from about 150° to about 250° of the annular portion.

7. The endovascular prosthesis defined in claim 2, wherein the annular portion spans 360 degrees of the tubular wall, and wherein the non-porous section radially spans from about 180° to about 240° of the annular portion.

8. The endovascular prosthesis defined in claim 2, wherein the non-porous section extends longitudinally a distance in the range of from about 2 cm to about 10 cm.

9. The endovascular prosthesis defined in claim 2, wherein the non-porous section extends longitudinally a distance in the range of from about 3 cm to about 8 cm.

10. The endovascular prosthesis defined in claim 2, wherein the non-porous section extends longitudinally a distance in the range of from about 3 cm to about 6 cm.

11. The endovascular prosthesis defined in claim 2, wherein the non-porous section comprises a cover material disposed over a fourth porous section.

12. The endovascular prosthesis defined in claim 2, wherein the non-porous section comprises a cover material connected to the first porous section.

13. The endovascular prosthesis defined in claim 12, wherein the cover material comprises a layer of polymer material.

14. The endovascular prosthesis defined in claim 2, wherein the tubular wall comprises a second porous section disposed adjacent one side of the annular portion and a third porous section adjacent an opposed side of the annular portion.

15. The endovascular prosthesis defined in claim 14, wherein the second porous section and the third portion section are interconnected by the first porous section.

16. The endovascular prosthesis defined in claim 2, wherein the tubular wall comprises a pair of radioopaque markers disposed at opposed ends of the non-porous section.

17. The endovascular prosthesis defined in claim 1, wherein the tubular wall comprises more than two interconnected expandable circumferential members.

18. The endovascular prosthesis defined in claim 17, wherein the circumferential members are interconnected by a plurality of longitudinal members.

19. The endovascular prosthesis defined in claim 17, wherein the circumferential members are interconnected by a cover material.

20. The endovascular prosthesis defined in claim 1, wherein the tubular wall comprises at least one radioopaque marker.

21. The endovascular prosthesis defined in claim 1, wherein the tubular wall comprises a pair of radioopaque markers disposed at opposed ends of the tubular wall.

22. The endovascular prosthesis defined in claim 1, wherein the tubular wall is constructed from a plastically deformable material.

23. The endovascular prosthesis defined in claim 22, wherein the plastically deformable material comprises stainless steel.

24. The endovascular prosthesis defined in claim 22, wherein the plastically deformable material comprises a laminar structure.

25. The endovascular prosthesis defined in claim 24, wherein the laminar structure comprises a layer of plastically deformable material and a layer of radioopaque material.

26. The endovascular prosthesis defined in claim 1, wherein the tubular wall is constructed from a self-expanding material.

27. The endovascular prosthesis defined in claim 26, wherein the self-expanding material comprises a shape memory alloy.

28. The endovascular prosthesis defined in claim 1, wherein, prior to the longitudinal expansion of said two adjacent undulating circumferential members, the covering material has a fold therein extending in a direction substantially orthogonal to a stent longitudinal axis.

29. A unitary, tubular endovascular stent having a longitudinal direction and a radial direction, comprising:
  first and second adjacent S-shaped annular members;
  a plurality of S-shaped longitudinal spines, each coupled to said first and second S-shaped annular members; and
  a covering material coupled to said first and second S-shaped annular members;
  said plurality of S-shaped longitudinal spines being longitudinally expandable prior to radial expansion of said plurality of S-shaped longitudinal spines; and
  said covering material having a longitudinal length that is greater than a longitudinal length between said first and second S-shaped annular members prior to the longitudinal expansion of said plurality of S-shaped longitudinal spines, said covering material including a fold substantially orthogonal to a stent longitudinal axis prior to the longitudinal expansion of said plurality of S-shaped longitudinal spines.

30. A cylindrical endovascular stent having a longitudinal direction and a radial direction, comprising:
  first, second, third, and fourth expandable S-shaped annular members;
  first and second expandable S-shaped longitudinal spines, each coupled to said first, second, third, and fourth expandable S-shaped annular members; and
  a non-porous material coupled to said second and third expandable S-shaped annular members;
  said first and second expandable S-shaped longitudinal spines being longitudinally lengthenable prior to radial expansion of said first, second, third, and fourth expandable S-shaped annular members; and
  said non-porous material having a longitudinal length that is greater than a longitudinal length between said second and third S-shaped annular members prior to the longitudinal expansion of said first and second expandable S-shaped longitudinal spines.

31. The cylindrical endovascular stent defined in claim 30, wherein, prior to the longitudinal expansion of said first and second expandable S-shaped longitudinal spines, the non-porous material has a fold therein extending in a direction substantially orthogonal to a stent longitudinal axis.

* * * * *